United States Patent [19]

Holtlund et al.

[11] Patent Number: 5,691,207
[45] Date of Patent: Nov. 25, 1997

[54] ANALYTE ASSAY USING SUPERAGGREGATED COMPLEX AS LABELLED REAGENT

[75] Inventors: Jostein Holtlund, Høvik; Geir Olav Gogstad, Oslo, both of Norway

[73] Assignee: Nycomed Pharma AS, Oslo, Norway

[21] Appl. No.: 39,426

[22] PCT Filed: Dec. 21, 1991

[86] PCT No.: PCT/EP91/02519

§ 371 Date: Apr. 29, 1993

§ 102(e) Date: Apr. 29, 1993

[87] PCT Pub. No.: WO92/11537

PCT Pub. Date: Jul. 9, 1992

[30] Foreign Application Priority Data

Dec. 24, 1990 [GB] United Kingdom ............... 9028038

[51] Int. Cl.$^6$ ................................. G01N 33/553
[52] U.S. Cl. .............. 436/525; 435/7.9; 435/7.92; 435/7.93; 435/7.94
[58] Field of Search ................ 435/969, 972, 435/7.9, 7.93, 7.94, 7.92; 436/531, 819, 525; 427/212, 216; 428/403

[56] References Cited

U.S. PATENT DOCUMENTS

| | | | |
|---|---|---|---|
| 3,853,987 | 12/1974 | Dreyer et al. | 436/533 |
| 4,279,617 | 7/1981 | Masson et al. | 436/819 |
| 4,313,734 | 2/1982 | Leuvering | 436/525 |
| 4,434,150 | 2/1984 | Azad et al. | 436/518 |
| 4,880,751 | 11/1989 | Geoghegan et al. | 436/525 |

FOREIGN PATENT DOCUMENTS

| | | |
|---|---|---|
| 0 007 654 | 2/1980 | European Pat. Off. . |
| 0 310 872 | 4/1989 | European Pat. Off. . |
| 0 317 001 | 5/1989 | European Pat. Off. . |
| 89 06801 | 7/1989 | WIPO . |

OTHER PUBLICATIONS

Geoghegan, *J. Clin. Immunoassay*, 11, 1, 1988, 11–23.
Goodman et al., *Scanning Electron Microscopy*, 11, 1980, 133–146.
Ghitescu, L. and Bendayan, M. Immunolabeling Effeciency of Protein A–Gold Complexes. Journal of Histochemistry and Cytochemistry 38(11): 1523–1530, 1990.
Dürrenberger MB. "Removal of Background Label in Immuno Histochemistry with Apolar Lonicryls by Using Washed Protein–A Gold–Precoupled Antibodies in a One–Step Procedure" Journal of Electron Microscopy Technique 11:109–116, 1989.

*Primary Examiner*—James C. Housel
*Assistant Examiner*—Gary Tanigawa
*Attorney, Agent, or Firm*—Bacon & Thomas

[57] ABSTRACT

Methods of assaying samples for the presence of an analyte involving immobilization of a gold sol, and optionally an enzyme capable of generating a reaction product, on a solid phase. The gold sol has a mean particle size of less than 20 nm for at least 75% by weight of the particles and is formed into a novel superaggregated complex with at least one protein.

26 Claims, 7 Drawing Sheets

ANALYTE ASSAY USING SUPERAGGREGATED COMPLEX AS LABELLED REAGENT

This invention relates to a method for the qualitative or quantitative determination of the presence of an analyte in an aqueous medium.

The detection and/or assay of analytes using immunoassay techniques is well established, particularly in relation to proteins such as antigens and antibodies, as well as sugars, lectins and nucleic acids. However, many current techniques, while being of great sensitivity, are often laborious in requiring a number of steps each of which may be of long duration. It has proved possible to simplify some of such assays, however, by immobilising one of the components of the assay system on a solid support, since this facilitates removal of excess reagents. Such assays will normally involve the use of a labelled macromolecule, which may be the analyte itself or a binding partner for the analyte, carrying a suitable label such as a radioisotope, a fluorophore or an enzyme producing a characteristic reaction.

One simplification which has been proposed is to use a coloured substance attached to one of the immunoassay reactants as a visible marker. However, very few coloured substances are able to produce a sufficiently intense signal. U.S. Pat. No. 4,313,734 of Akzona Inc. describes the use of, inter alia, colloidal gold as such a coloured material, specifying that the gold particles should have a particle size of at least 5 nanometers, preferably 10 to 100 nm.

An improved immunoassay system is described in WO89/06801 in which at least 75% of the gold particles have a mean diameter of less than 5 nanometers. This is said to give more rapid reaction of the gold reagent with the immobilised reactant together with an increase in colour intensity. We have now found that a yet further increase in colour intensity may be obtained when the very small gold particles of WO89/06801 are formed into larger particles (superaggregated gold-protein colloids) by a novel aggregation process. The superaggregated particles are very different from the monolithic gold particles used in immunoassays to date and allow for analysis of substances at even lower concentrations than the already impressively low levels made possible by the systems of WO89/06801.

Small gold particles are also used as markers in a blotting system, as described in U.S. Pat. No. 4,775,636 of Janssen Pharmaceutica N.V. However, there is no suggestion that the particles are aggregated, rather they are simply bound to the component which it is desired to visualise.

According to the present invention we provide a method for the qualitative or quantitative determination of an analyte in a test sample wherein a labelled reagent comprising a gold sol bound to a substance capable of specifically binding to said analyte or to a specific binding partner therefor, is caused to be immobilised in bound form on a solid phase to provide an indication of the presence or quantity of the analyte in the sample, characterized in that the labelled reagent comprises a superaggregated complex of said substance or specific binding partner therefor and a gold sol wherein at least 75% by weight of the gold particles of the gold sol have a mean diameter of less than 20 nanometers.

In many types of solid phase assay it is advantageous to couple an analyte analogue or a specific binding partner for said analyte to a solid support to provide the solid phase onto which the labelled reagent is immobilised. As a further aspect of the invention therefore, we provide a method for the qualitative or quantitative determination of an analyte in a liquid sample, wherein said sample is contacted in an aqueous assay medium with (i) an analyte analogue or a specific binding partner for said analyte immobilised on a solid support and (ii) a labelled reagent comprising a gold sol attached to a molecule capable of specifically binding said analyte or a specific binding partner therefor, and optionally an enzyme capable of generating a characteristic reaction, whereby a quantity of said labelled reagent is immobilised on said support, inspection or determination of the colour of which and/or the colour generated by said enzyme when exposed to a substrate therefor is used to indicate the presence or quantity of the said analyte in the sample, wherein the labelled reagent comprises a superaggregated complex of said substance or specific binding partner therefor and optionally said enzyme, and a gold sol wherein at least 75% by weight of the gold particles of the gold sol have a mean diameter of less than 20 nanometers.

The solid phase onto which the labelled reagent is immobilised may alternatively be inert and immobilise the bound form of the labelled reagent by trapping the latter physically, e.g. by not allowing the bound form of the labelled reagent to pass through pores in the solid phase, while allowing the unbound labelled reagent to pass through such pores.

The term "analyte analogue" as used herein will be understood to refer to any species capable of specifically binding to a specific binding partner for the analyte under assay and thus includes within its scope a further quantity of that analyte.

The mean diameter of a particle, which may not be completely spherical, is the mean of the largest and smallest diameters of that particle. It is preferred that at least 75% by weight of the gold particles forming the superaggregated complex have a mean diameter less than 5 nm and particularly preferred that at least 80% of the gold particles are below this limit. A lower limit for the mean diameter of the particles is conveniently 1 nm. Certain batches of the product Colloidal Gold Sol G5 of Janssen Life Sciences Products, sold for use as a histological stain, have proved to be useful. In one specific batch, 85% of the particles were less than 5 nm in diameter, the average diameter being 4.5 nm with a Gaussian distribution between 1.1 and 7.6 nm. Gold sols with average diameters in the range 2–4 nm may also conveniently be made by slight modifications of known methodology, e.g. variation of tannic acid concentration in the procedure of Slot and Geuze (Eur. J. Cell. Biol. 38, 87–93, 1985). We have found that particles having a mean diameter of 4–4.5 nm are preferable.

The superaggregated complexes may be formed from the gold sol and the reagent to be labelled (protein) by mixing the desired quantities of both in solution, adjusting the pH to 1–5, preferably 3–4 and more preferably 3.5, by addition of acid, for example, acetic acid to a final concentration of about 10 mmol/l, and collecting the macroscopic aggregates so formed by filtration with washing, or alternatively by repeated centrifugation and resuspension. The macroscopic aggregates are resuspended in a pH-neutral medium, for example containing 2% bovine serum albumin (BSA) by weight, with optional ultrasonic treatment. The macroscopic aggregates surprisingly disappear rapidly and leave a suspension of stable superaggregated gold-protein complexes.

Superaggregated colloids may also be formed with some proteins at a neutral pH provided that the colloids are in molar excess to protein, and that the protein used exhibit a certain number of positively charged groups (>2) at the actual pH used. However, an acidic pH normally produces the best results.

The superaggregated complexes used in the methods according to the invention are conveniently 50–5000 nm nanometers in size, preferably 50–500 nm and most preferably 100–200 nm. The number of gold sol particles per complex will obviously depend on the particle size and complex size, but an example may be given where 5 nm particles are spaced 10 nm apart by intervening protein molecules. Under such circumstances a 50 nm complex will contain about 15 particles and a 5000 nm complex about 20 million particles. A 200 nm complex was observed to contain about 1000 particles which is consistent with the 10 nm inter-particle spacing.

The superaggregated gold complexes obtainable by the above described processes, and the processes for forming them, are novel and as such form yet further aspects of the invention.

By contrast with the above described processes, the normal way of performing protein-gold conjugation is to transfer the protein to a low-salt medium with a pH close to the pI for the protein. Normally the pH is recommend to be one pH-unit above the pI. In this situation the protein possesses a minimum of positively charged chemical groups. When this solution is mixed together with gold colloids which are believed to have a massive surface-localization of electrons, only a few bonds between the protein and the colloid are established. In this situation, the formation of bridges between a multiple of proteins and colloids is avoided, and the colloids will be kept in solution as single particles covered by protein molecules.

When the pH in the protein solution is lowered, the number of positively charged groups on each protein molecule increases. Thus, the number of possible ionic bonds between protein and colloid increases, leading to formation of multiple bridges and formation of macroscopic aggregates. This is normally regarded as a highly unfavourable situation which should be avoided. However, the present invention takes advantage of this effect. When a further addition of protein is made, the macroscopic aggregates surprisingly dissolve and leave a solution of uniformly sized superaggregates of protein and gold colloids. Since the colloids are spaced by protein molecules, we believe the surface to be greatly increased in each superaggregate. Since it is believed that the colour formed by the metal colloids is a physical phenomenon related to the surface of the colloids, the massive increase in the signal is probably caused by a correspondingly massive increase in total surface per superaggregated complex.

By way of illustration of the improvements realised by the present invention, the colour intensity using superaggregated complexes containing a binding partner for an analyte immobilised on a solid matrix can be 5–30 times greater than the colour observed using a 4 nm gold-antibody conjugate according to WO89/06801, depending on the precise system used.

It is possible to form superaggregated gold complexes containing two or more types of protein molecule thus giving a number of options for increasing the flexibility and sensitivity of the assay methods according to the invention. One possibility is to aggregate the substance capable of binding the analyte (or specific binding partner therefor) and an enzyme capable of generating a characteristic reaction into a superaggregated complex. This gives the possibility of determining the presence or quantity of the analyte by inspecting or determining the colour of the gold sol and/or by exposing the enzyme to a substrate and inspecting or determining the colour generated by the enzyme. When the colour of the gold sol is below the measurable detection limit, the enzyme may give a detectable colour upon prolonged incubation with a suitable substrate. Examples of suitable enzymes are alkaline phosphatase and peroxidases such as horseradish peroxidase. It will be appreciated that when the colour of the gold sol is below the detectable limit for analyte determination then the gold sol superaggregate is acting as a particularly mild form of protein-protein cross linking which will have advantages in certain circumstances compared to conventional covalent cross linking.

Alternatively a superaggregated complex containing two substances capable of binding to different target molecules may be formed, for example on the one hand an antibody (Ab1) for the analyte and on the other hand an antibody (Ab2) for a different antigen. Once the complex is bound via Ab1 to the analyte, itself bound directly or indirectly to a solid support, then exposing the whole to a further superaggregated complex containing the antigen (Ag2) for antibody Ab2 will cause a cluster of second complexes around the first complex and an increase in the total gold sol colour. The process could be continued for further stages if desired, for example the second complex could contain two antigens Ag2 and Ag3, the latter serving as an attachment point for a yet further complex containing an antibody therefor (Ab3).

Other receptor-ligand pairs can of course be envisaged in such an amplification system such as (strept)avidin and biotin, enzymes and enzyme inhibitors, lectins and glycoproteins, protein A and immunoglobulins, and so on.

The system may also be brought to form growing complexes of aggregates by simultaneous addition of two hybrid aggregates one of which can be bound to an immobilized analyte receptor, and both carrying multiple reacting groups of at least two types each, one of which interacts with the other aggregate. The result will be the formation of a network of aggregates which can be formed in a dose-dependent way if the material is added to a flow-through system carrying the immobilized analyte.

Gold colloids aggregated with an antibody reacting with an analyte antigen may agglutinate upon addition of the analyte. This reaction may be slow. An amplification may be achieved by forming a hybrid first aggregate based on gold colloids and a first antibody Ab1 reacting against the analyte antigen Ag1, and a second antibody Ab2. A second aggregate carrying multiple antigens Ag2 reacting with Ab2 is added and will speed up the agglutination reaction.

The methods according to the present invention can be applied to any solid phase system for detection or assay of analytes. The following types of assay are typical:

1. A sandwich assay in which component A is bound to a solid support. Test solution with analyte B is added whereby B binds to A. Gold-labelled component C is added and since C binds to B the colloidal gold is immobilised and colours the solid support.
   Components A, B and C are all of receptor-ligand types in which both A and C interact with B, whereas A and C do not directly bind to each other.
2. A sandwich assay as in 1 except that the test solution with analyte B and gold-labelled component C are mixed and the mixture is added to the solid support to which component A is bound.
3. A competitive assay in which component A is bound to a solid support. Test solution with analyte B is mixed with a known amount of gold-labelled analyte B and added to the solid support. B and gold-labelled B will compete in binding to A and a reduction of the colour of colloidal gold on the solid support indicates increasing amounts of analyte B in the test solution.
4. A competitive assay as in 3, but sequential addition of test solution and gold-labelled B.

5. Excess component A is labelled with colloidal gold and mixed with test-solution containing unknown amount of analyte B. A and B then couple. The mixture is added to a porous support onto which component B is immobilized. Remaining, unbound labelled A will couple to the immobilized B on solid support.
6. Analyte B is reacted with gold labelled component C, optionally together with one or more other binding partners for analyte B to form a complex aggregate. The reaction mixture is caused to diffuse through an inert filter medium, the pores of which are too small to allow the complex aggregate to pass through but large enough to permit excess gold labelled component C to pass through.

The solid phase or support on to which the labelled reagent is caused to be immobilised can take a number of forms, of which the following are illustrative:

A plastic stick, optionally covered with pads of any porous material. The stick may be dipped in the reaction solutions in order to conduct the various steps of an assay.

The wall of a test tube, a well in a microtitre-plate or the wall of any other suitable reaction chamber.

A porous material, conveniently a membrane, in which the reaction solutions may diffuse transversely through or laterally. In the case using the filtration principle, such materials advantageously permit excess reagents to pass through and may conveniently be combined with an absorbent for such excess liquids.

Beads (including microspheres) which may be isolated by centrifugation, filtration or, where the beads contain ferromagnetic compounds, magnetism.

The coupling of the analyte analogue or specific binding partner for the analyte under assay to the support may be by covalent, electrostatic or hydrophobic means or a combination of these methods. Such methods are well established in the art.

The method of the invention may be used to detect or assay a wide range of analytes which may be selected, for example, from the following ligand-receptor pairs: antigen/antibody, hapten/antibody, hormone/hormone receptor, sugar/lectin, biotin/avidin-(streptavidin), protein A/immunoglobulin, enzyme/enzyme cofactor, enzyme/enzyme inhibitor and nucleic acid pairs (DNA-DNA, DNA-RNA or RNA-DNA). At least one of such reaction partners may be bound or complexed with other molecules. Thus, biotin or avidin or a wide range of antibodies may be coupled to other molecules to provide a means of assaying the latter. For example, a specific nucleic acid probe can be labelled via the introduction of biotinylated nucleoside triphosphates. Such a probe, after binding to analyte DNA or RNA, can then be detected or assayed by the use of avidin or streptavidin labelled with gold sol.

In general, where the analyte is one of those listed above, a binding partner for use in the method of the invention will be the other component of the pair. In sandwich systems wherein the analyte binds both to an immobilised binding partner and a binding partner labelled with gold sol, the binding partners may be the same or different. Preferably the binding partners will each be an antibody reagent directed against different, well spaced determinants of the analyte.

It will be understood that the term "antibody" as used herein includes within its scope (a) any of the various classes or sub-classes of immunoglobin, e.g. IgG, IgM, derived from any of the animals conventionally used;
(b) monoclonal antibodies; and
(c) fragments of antibodies, monoclonal or polyclonal, which retain an antigen-binding site, i.e. fragments devoid of the Fc portion (e.g Fab, Fab', F(ab'))$_2$) or the so-called "half-molecule" fragments obtained by reductive cleavage of the disulphide bonds connecting the heavy chain components in the intact antibody.

Below is a non-exhaustive list of the types of immunogens which can be detected or quantified by the method of the present invention.

| | |
|---|---|
| proteins | glycoproteins |
| nucleoproteins | peptide hormones |
| serum proteins | complement proteins |
| coagulation factors | microbiocidal products |
| viral products | bacterial products |
| fungal products | specific Immunogens |
| albumin | angiotensin |
| bradykinin | calcitonin |
| carcinoembryonic antigen | creatinine kinase isoenzymes |
| chloriomamotropin | chorogonadotropin |
| cortiocotropin | erythropoietin |
| Factor VIII | fibrinogen |
| alpha-2-H-globulin | fibrin degradation |
| follitropin | products |
| Gastrin | gastrin sulfate |
| glucagon | gonadotropin |
| haptoglobin | Hepatitis B surface |
| immunoglobulins | antigen |
| (A,D,E,G,M) | human C-reactive |
| insulin | protein |
| kallidin | lipotropin |
| melanotropin | myoglobin |
| oxytocin | pancreozymin |
| placental lactogen | prathryin |
| proangiotensin | prolactin |
| somatotropin | relaxin |
| secretin | somatomadin |
| somatostatin | thryrotropin |
| thymopoietin | vasotocin |
| vasopressin | |
| alpha-1-fetoprotein | alpha-2-H globulin |

Particularly interesting analytes for assay by the method of the invention are blood proteins such as fibrin degradation products e.g. $D_2$, which are bound by immunoglobulins such as IgG; human c-reactive protein; creatinine kinase isoenzymes; and myoglobin.

The analyte solution may be used directly or may be diluted, e.g. with a suitable buffer solution. The gold sol preparation may also be prepared at varying dilutions using an appropriate buffer solution, the dilutions being selected to give a colour of desired intensity (i.e. optical density or reflection) on completion of the assay procedure. It may be desirable to wash the support to remove excess reagents, e.g. with a buffer solution prior to assay, in order to reduce background colour.

Where the assay is based on the total amount of gold sol retained on the immobilised support, the colour may be estimated by a reflectometer, densitometer or similar device.

The support used to immobilise one of the binding partners in the assay or an analyte analogue may, for example, be nitrocellulose, paper or cellulose acetate activated with reagents such as cyanogen bromide and nylon modified by introduction of tertiary amino groups. Such supports are conveniently used in the form of porous membranes.

In a particularly preferred method according to the invention, the inert support is a membrane, for example a nylon membrane such as Hybond N (sold by Amersham International) which readily adsorbs proteins and which has pores which permit passage of liquid. An absorbent pad such as cellulose blotting paper is advantageously placed on one side of the membrane and a liquid impermeable sheet, preferably white, placed over the pad. A similar liquid impermeable sheet is placed over the other side of the membrane, a hole, e.g. about 3.5 mm wide, being provided in this sheet to permit application of analyte solution and assay liquids to the membrane. Initially, the membrane is activated by application of a small volume, e.g. about 2 µl, of an aqueous solution containing a known quantity of binding partner for the analyte, followed by drying e.g. by leaving to dry at room temperature. A known volume of the aqueous solution containing the analyte, e.g. about 25 µl, is then applied to the membrane and allowed to pass through into the absorptive pad beneath. An aqueous solution, e.g. 25 µl, containing a known quantity of colloidal gold sol particles labelled with a binding partner for the analyte, which may be the same as or different from that initially applied to the membrane, is then applied and allowed to pass through the membrane.

A small volume of water or buffer may optionally be applied to wash through the gold sol reagent and thus minimise background colour. The quantity of gold sol immobilised on the membrane is then determined by a reflectometer or by the naked eye by comparison with a colour-scale.

In the operation method (6) set out above, the membrane may be sheet material of the desired porosity which may be inert insofar as its only function is to act as a filter. The aggregation of the analyte with the component C may be enhanced by including two or more different binding partners for the analyte to effect a form of cross-linking leading to larger aggregates. Alternatively, the component C may comprise the binding partner for the analyte immobilised on beads, for example mono-disperse beads such as Dynospheres (Dynal A/S, Oslo, Norway).

The invention also includes kits for carrying out the method of the invention comprising (a) a solid phase onto which a labelled reagent is caused to be immobilised to provide an indication of the presence or quantity of the analyte in the sample and (b) a labelled reagent, characterized in that the labelled reagent comprises a superaggregated complex of a substance capable of specifically binding to said analyte or to a specific binding partner therefor and a gold sol wherein at least 75% by weight of the gold particles of the gold sol have a mean diameter of less than 20 nanometers. A preferred form of kit comprises (a) a solid support for immobilisation of an analyte analogue or a specific binding partner for the analyte or a complex of the analyte with one or more other reagents, (b) said analyte analogue or binding partner and (c) a reagent comprising a superaggregated complex of a molecule capable of specifically binding to the analyte or a specific binding partner therefor and a gold sol wherein at least 75% of the particles of the gold sol have a mean diameter less than 20 nm. When an enzyme capable of generating a characteristic reaction is included in the superaggregated complex then a supply of the enzyme substrate can also be included in the kit.

Optionally, the solid phase contained in the kit may be a solid support ready for contacting with the analyte by the user, by preliminary coupling of an analyte analogue or a specific binding partner for the analyte to the support. For some assays, such a kit may include a standard amount of the analyte, a standard amount of a specific binding partner therefor and the gold sol reagent. Standard amounts of analyte or specific binding partner or reagent may be in the form of aqueous solutions or, more usually, lyophilised preparations adapted for dissolution at the time of use. In one form of assay, the solid support may be an inert porous membrane which serves to retain a complex of the analyte and a binding partner in aggregated form but permits diffusion of the gold sol reagent, as in method 6 above. In such a system, the size of the analyte complex may be increased by providing said binding partner or analyte analogues attached to relatively large particles e.g. Dynospheres as mentioned above.

While the foregoing discussion and the following examples concentrate on receptor-ligand assays, it will be appreciated that the novel superaggregated complexes will have a wide variety of other uses in areas where gold colloids have found application. Thus the aggregates may be used in blotting techniques when linked to an antibody or other binding material directed against a compound suspected to be present in a sample; they will also be useful in staining tissue sections for light or electron microscopy and for other staining techniques; in centrifugation they will be useful as markers; and in agglutination assays they may replace the latex particles currently used. Other applications may readily be envisaged by those skilled in the art where the superaggregated complexes may replace other types of particle currently used.

The following Examples are given by way of illustration only:

EXAMPLE 1

Colloidal gold with an average diameter of 4 nm was produced as described in Mulphfordt (1982), Experientia 38, pp 1127–1128).

A mouse monoclonal antibody S4H9 directed against the fibrin degration product D-dimer was developed by ordinary hybridoma technology, the antibody was produced in mouse ascites, and finally purified. Before use, the purified antibody was dialyzed against distilled water and adjusted to a concentration of 1.5 mg/ml.

Figure 1A:
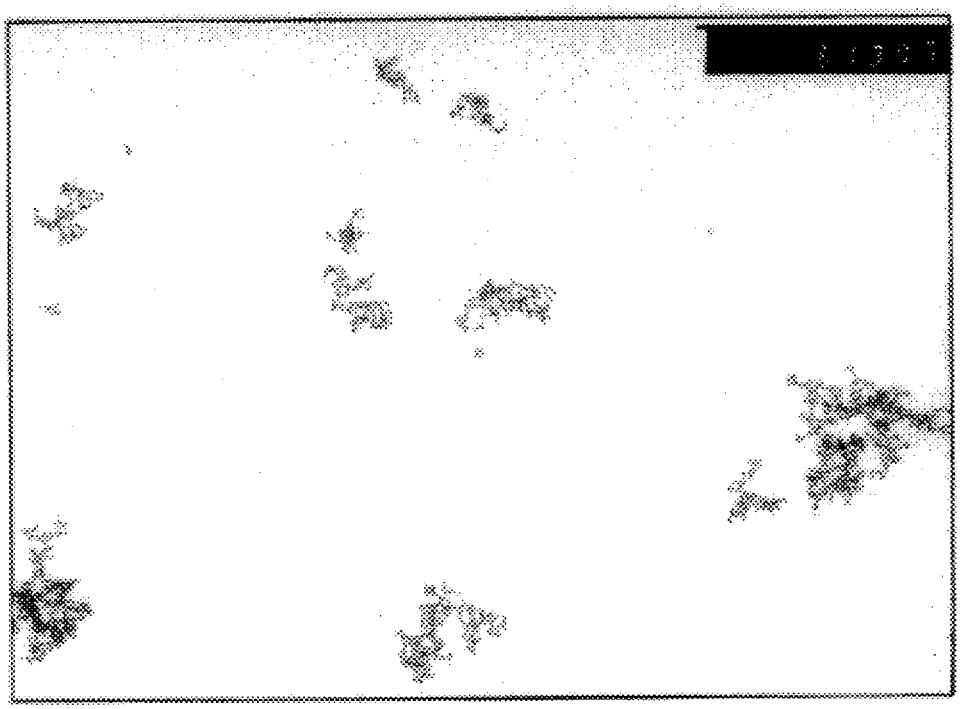
FIGS. 1A and 1B are electron micrograph revealing that the colloids were present as clusters with diameters 100–200 nm.
Figure 1B:
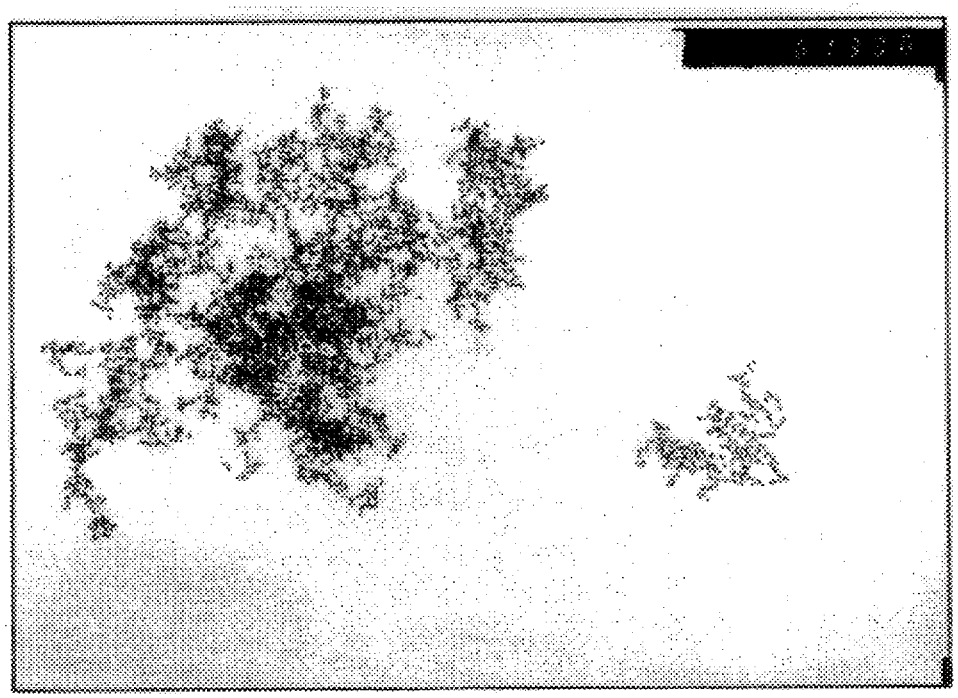

A suspension of gold colloids having an optical density of 40 at 540 nm (estimated from dilution of the colloid-suspension) was used. The suspension was prepared by centrifugation, removal of 90–95% of the supernatant, and resuspension is distilled water, prior to use. To 25 ml of this solution was added acetic acid to a final concentration of 10 mmol/l giving a pH of about 3.5, immediately followed by the addition of 15 ml of the dialyzed solution of antibody S4H9. The mixture was stirred for 20 minutes. Macroscopic aggregates were immediately visible. After 20 minutes the suspension was centrifuged at 5000×g for 10 minutes. The supernatant was removed and the sedimented aggregates were resuspended in distilled water to a final volume of 40 ml. 10 ml of a solution of 10% bovine serum albumin (BSA) was added. The suspension was cooled on ice and then subjected to gentle ultrasonication for about 15 seconds. Larger volumes can preferentially be sonicated in a flow-system. The suspension was diluted four times to a final volume of 200 ml, subjected to sterile filtration in a 0.22 micrometer filter, and finally adjusted to 20 mmol/1 NaCl. Electron microscopy revealed that the colloids were present as clusters with diameters 100–200 nm (FIG. 1).

The suspension passed the 0.22 micrometer filter, (=220 nm), whereas filters with diameters 100 nm and 50 nm completely arrested the coloured colloids.

Figure 2:
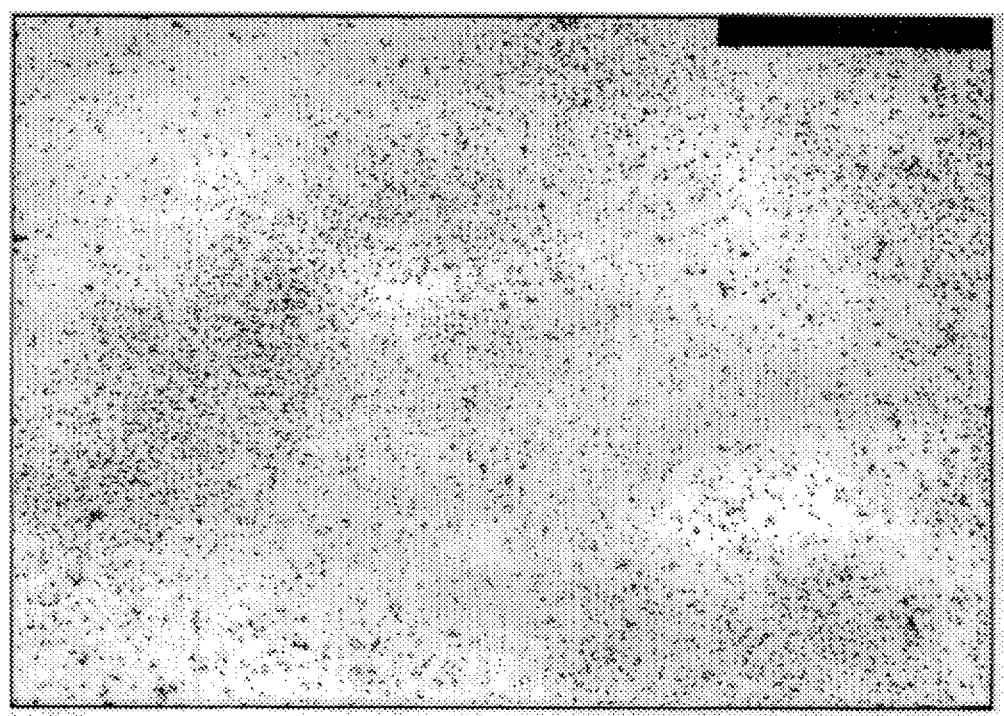
FIG. 2 is an electron micrograph of gold particles randomly distributed in solution.

A standard conjugate was made using the standard labelling method for antibodies as described by Slot and Geuze (Eur. J. Cell. Biol. 38, pp 87–93, 1985). In this procedure, no aggregates were formed since the pH was kept close to the pI of the antibody under the conjugation procedure. Estimated ratio between gold and antibody in the resulting conjugates was 1:1, and electron microscopy verified that the gold particles were randomly distributed in solution (FIG. 2).

The conjugates were tested in the following test device:

A 1×1 cm piece of nitrocellulose membrane with pore size 0.6 μm was placed under a strip of white polyvinyl chloride (PVC), 0.28 mm thick, and with a 3.5 mm hole centred over the membrane. The membrane was attached to the plastic using double sided tape. The PVC-strip with the attached membrane was then attached to a 1 mm thick pad of cellulose paper to the tape area not covered by the membrane. The device was closed underneath by another strip of PVC, 0.40 mm thick, fixed to the pad using double sided tape. This construction makes it possible for liquid to pass through the hole in the upper PVC-strip, through the membrane, and accumulate into the pad. The membrane was activated by adding 2 μl of a 3.0 mg/ml solution of antibody S4H9 and the membrane was allowed to dry before further use.

25 μl of plasma sample known to contain D-dimer were applied to the membrane surface in parallel holes in the test device. After about 20 seconds the plasma had passed through the membrane and into the pad. 25 μl of gold conjugate of the aggregated form, and the 25 μl of gold conjugate of the non-aggregated form were added to each of the two parallel holes. When the liquid had passed the membrane, a drop of 0.15 mol/1 NaCl was added to wash out excess of conjugate. As a control, plasma known to contain normal, low levels of D-dimer was subjected to the same procedure using the two conjugates. The results were instrumentally read by employing a reflectometer (Color Eye, Macbeth), attached to an IBM PC and using Macbeth's software program.

The results obtained showed that the colour formed with the normal plasma with low level of D-dimer, produced an equal low reflectance <0.18 at 540 nm. The colour formed with the non-aggregated conjugate was generally weak, whereas the colour formed with the aggregated conjugate was about ten times stronger as judged from the reflectance values. The results show that the new form of conjugates produced a net result which was markedly stronger than with the ordinary conjugates. The background signal was not affected by the aggregation.

Furthermore, the filtration test show that the size of the aggregated gold colloids was in the range 100–200 nm. This was verified by electron microscopy.

EXAMPLE 2

In this example it is demonstrated that aggregated conjugates also may be formed using a simpler method without sonication.

Gold colloids, test device and antibodies were made as described in example 1. The gold colloid suspension was prepared as described to the level of adjusting the pH to 3.5 using acetic acid. 25 ml of the pH-adjusted colloid-suspension was added to 12.5 ml of a solution of 1.5 mg/ml of S4H9. After 25 minutes at 20° C., the suspension was added a solution of 10% BSA adjusted to pH 9.0. The final concentration of BSA was 0.2%. The suspension was then adjusted to 40 mmol/l Tris-HCl (pH 7.3). When the suspension was left stirring overnight, the visible aggregates disappeared, and the suspension passed a sterile filter with pore size 0.22 μm, but not a 100 nm filter. Electron microscopy revealed that aggregates were formed, although not as tightly packed as in the procedure described in example 1. Testing according to the scheme in example 1 revealed that the signal was increased by about five times compared to ordinary, non-aggregated conjugates.

EXAMPLE 3

The procedure in example 1 was repeated with the only exception that the gold colloid suspension was added NaCl to 5 mmol/l and kept at 4° C. for 14 days before use. This procedure makes the gold colloids form aggregates in a more prominent way. When the conjugates were tested according to the scheme in example 1, the colour signals were about thirty times as strong as the signals obtained using non-aggregated gold. The background level was slightly increased indicating that the aggregates formed exhibited larger diameters.

EXAMPLE 4

In this example, it is demonstrated that certain antibodies may form aggregates with gold colloids at pH close to neutral. The size and signal intensity that arise from the use of such aggregates may be adjusted by varying the ratio between protein and gold in the conjugation procedure.

A mouse monoclonal antibody termed 2D2, specific towards human serum albumin, was developed using the well-known hybridoma technology. The antibody production was scaled up using mouse ascites fluid techniques, the antibody was purified, and dialyzed against 2 mmol/l sodium phosphate buffer (pH 6.8). The final concentration of antibody was 1.0 mg/ml.

Gold colloids were made as described in Example 1. The colloidal suspension was adjusted to optical density 40 at 540 nm.

Antibody solution and gold colloid suspension were mixed in the following ratios: 1+2, 1+2.2, 1+2.5, 1+3, 1+3.5.

After 25 minutes at 20° C., the solutions were added an equal volume of 1% BSA-solution.

The conjugates were tested in devices as described in example 1. The membranes were activated by addition of 2 μl of a 3.0 mg/ml solution of another mouse monoclonal antibody (2D3) directed against human serum albumin. The membranes were allowed to dry before use.

Human urine samples with albumin added to 0(control), 10, 25, 50, 100 and 200 mg/l respectively were diluted in 0.15 mol/l of NaCl in the ratio 1+20. 25 μl of each dilution was added to five parallel holes in the test devices. When the diluted samples had sucked into the membrane, one drop of each of the conjugates was added to each hole in each of the parallel series. Finally, one drop of 0.15 mol/l NaCl was added to wash the membrane, and each hole was read reflectometrically as described in example 1.

Figure 3:
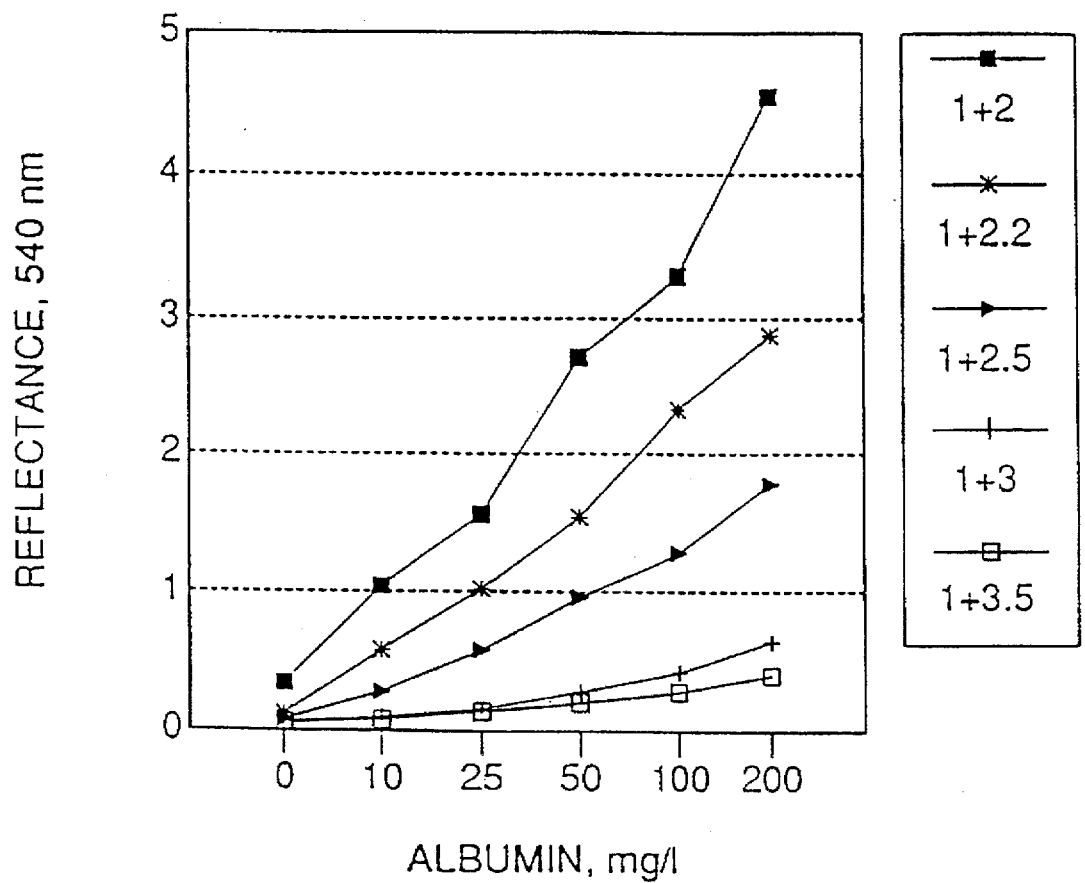
FIG. 3 illustrates the dose-response curves obtained at various ratios of antibody solution to gold colloid suspension.

The results are shown in the FIG. 3, showing that there is a marked increase in the resulting signal when the amount of antibody increases. In none of the cases could free antibodies (not conjugated to gold particles) be found in the solutions. Because of this, and because of the relative increase in reflectance values, the increase in signal cannot be explained by an increased number of reacting antibodies as such. Experiments with 50 nm filters also showed that the 1+2 ratio conjugate was mainly arrested by the filter, whereas the 1+3.5 ratio conjugate passed freely. Thus, aggregates with increased ability to raise the signal had been formed with antibody 2D2 at pH close to neutral.

EXAMPLE 5

The procedure of example 1 was repeated, with the only exception that the antibody was replaced with a monoclonal antibody T11G8 directed against C-reactive protein. The concentration of antibody, the solvent for the antibody, the colloidal gold, and the entire procedure was the same as in example 1. The filtration test showed passage through 200 nm filters, but not in 50 or 100 nm filters.

For comparison, a standard conjugate was made keeping the pH at 6.5 which is close to the pI of T11G8. This conjugate readily passes a 50 nm filter indicating that aggregates were not formed. Electron microscopy verified this, showing only minor clustering of gold colloids in the final preparation.

The two conjugates were tested in a device similar to that described in example 1. The membrane was activated by addition of 2 microliters of a 3.0 mg/ml solution of monoclonal antibody G405 directed against C-reactive protein and dried before use. 25 µl of diluted plasma samples known to contain C-reactive protein was applied to each piece of membrane through the aperture in the plastic cover, followed by 25 µl of conjugate solution in either of the two forms prepared, and further one drop of 0.15 mol/l NaCl to remove background colour.

Figure 4:
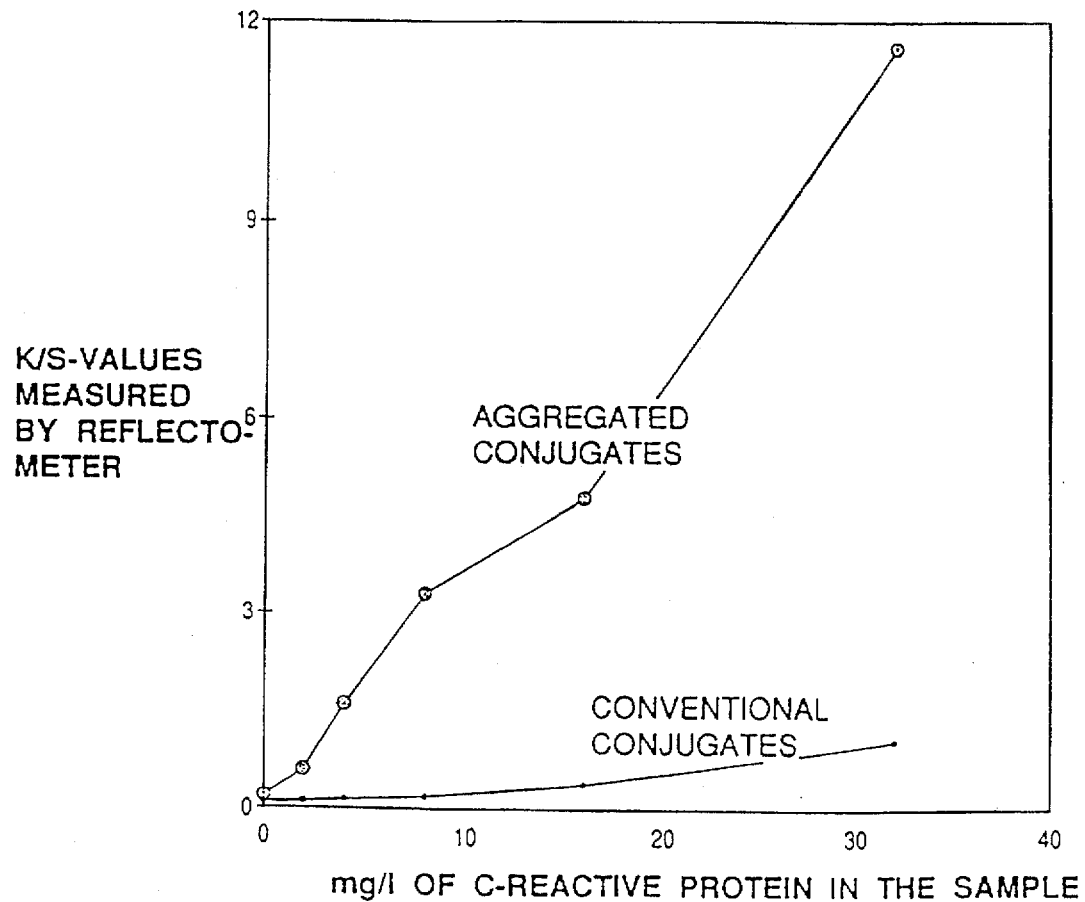
FIG. 4 show the results obtained by serial dilutions from 1:50 to 1:800 of a plasma containing 32 mg/l of CRP.

FIG. 4 show the results obtained by serial dilutions from 1:50 to 1:800 of a plasma containing 32 mg/l of CRP. The diluent was 0.15 mol/l NaCl. As the figure shows, the two types of conjugates demonstrate considerably different staining intensity on the membrane, the aggregated conjugate resulting in more than ten times increased signals.

Both conjugates were kept at 4° C. for a period of nine months and tested regularly. None of the conjugates showed altered properties after this time of storage, indicating that the aggregated conjugates are extremely stable.

EXAMPLE 6

The experiment above was repeated by replacing antibody T11G8 with a purified rabbit anti-human serum albumin (anti-HSA). The resulting conjugates were tested in a device containing membranes coated with a monoclonal anti-HSA antibody using the same procedure as in examples 1 and 5. The results showed that when applying diluted urine known to contain albumin, the aggregated conjugate resulted in about eight times increased colour signal compared to the conventional non-aggregated conjugate.

EXAMPLE 7

Aggregated conjugates can also be formed using proteins different from antibodies. The procedure of preparation of gold colloids and aggregated conjugates from example 1 was repeated, this time replacing the antibody with bovine serum albumin. The albumin concentration used was 1.5 mg/ml, as with the antibodies. Aggregates with properties in filters similar to the antibody-aggregates were formed. The albumin-aggregated colloidal gold was examined by electron microscopy and demonstrated a random distribution of clustered colloids similar to those formed in example 1.

EXAMPLE 8

Another protein different from antibodies which can be conjugated to colloidal gold in an aggregated form, is Protein A. The same procedure as in example 1 was used, using protein A concentration of 1.5 mg/ml as with the other proteins. The resulting aggregated conjugate as well as a conventional, non-aggregated was tested in a device similar to that described in example 1. The membrane was coated with a monoclonal IgG antibody directed against human serum albumin. Since protein A reacts directly with immunoglobulins, the addition of various dilutions of the two conjugates showed that upon addition of an equal amount of conjugated protein A, the aggregated conjugate produced a signal which was about twelve times stronger than the signal obtained with the conventional conjugate.

EXAMPLE 9

In this example is demonstrated the formation of a hybrid aggregate containing two different proteins which can be used for binding and signal formation, respectively. The enzyme alkaline phosphatase (ALP) is co-conjugated to gold particles together with rabbit anti-mouse IgG. Such a conjugate allows detection of mouse IgG's either by directly observing the gold stain, or by making use of the enzyme in an ELISA-manner.

The enzyme (ALP) and the antibody were desalted by gel filtration on a PD-10 column equilibrated with 10 mmol/l acetic acid, and subsequently mixed in a mass ratio of 1.5:1 (enzyme:antibody). The protein mixture was then conjugated to gold colloids in 10 mmol/l acetic acid, the sum of the masses of the two proteins amounting to the same protein:gold ratio described in example 1. The superaggregated, precipitated conjugates were allowed to sediment passively, sonicated and blocked with bovine serum albumin (BSA), and finally sterile filtered, the whole procedure taking about one hour.

Figure 5:
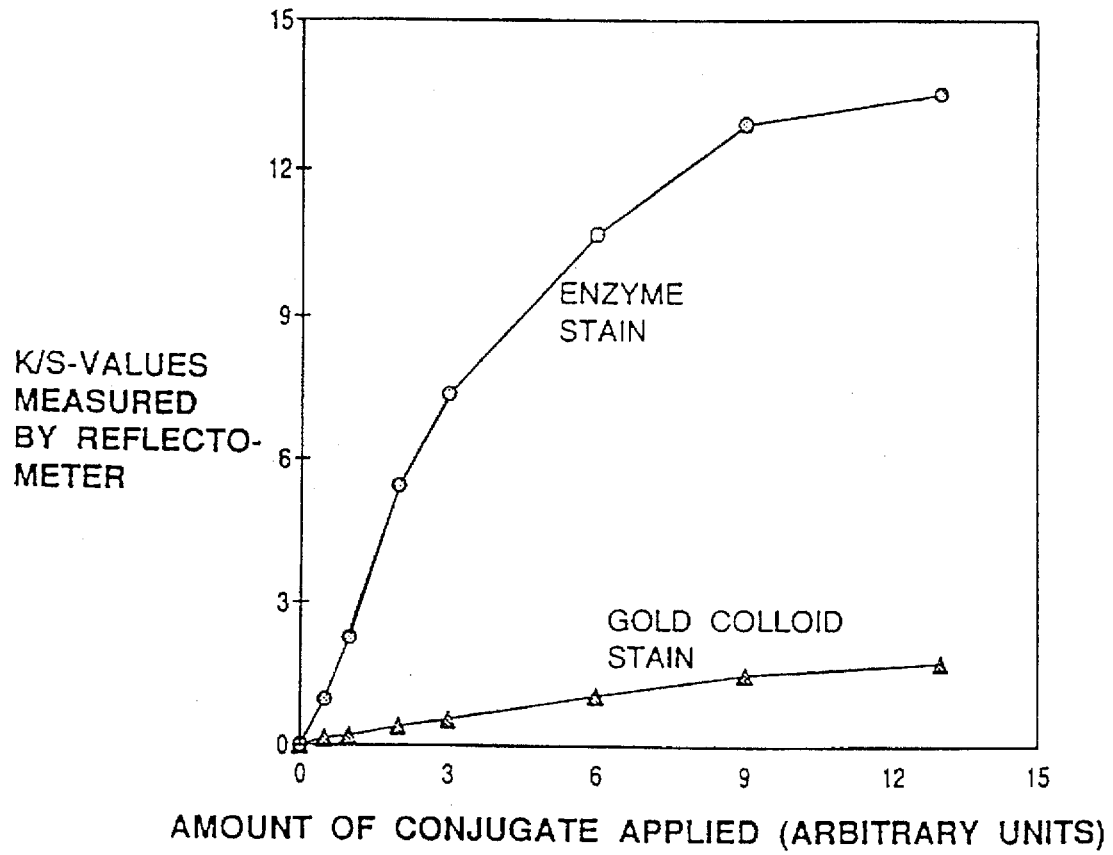
FIG. 5 demonstrates the detection potential of the resulting hybrid conjugate.

FIG. 5 demonstrates the detection potential of the resulting hybrid conjugate. Dilutions of the conjugate were dotted directly onto nitrocellulose with an even distribution over circles with diameter 3.5 mm. The gold stains were measured by means of a reflectometer. The nitrocellulose was subsequently transferred to an alkaline phosphatase substrate solution containing bromochloroindolylphosphate (BCIP). After incubation with gentle shaking for 30 minutes, a dark, purple product from the ALP's action on BCIP precipitated on the nitrocellulose. FIG. 5 shows that a further increase in sensitivity of ten times over that obtained with the gold stain was achieved by utilizing this optional enzyme activity.

Figure 6:
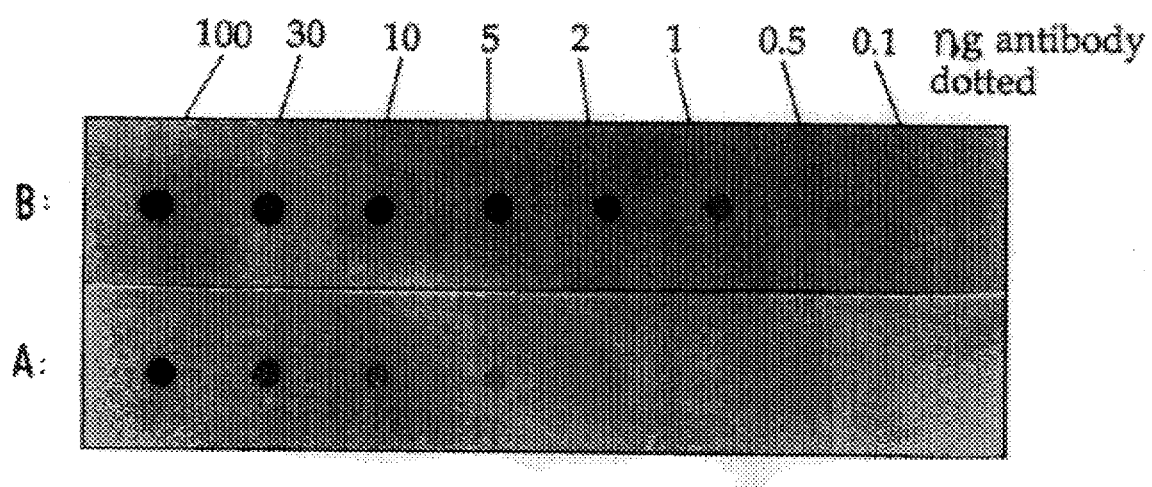
FIG. 6 shows the detection of a mouse monoclonal IgG dotted onto nitrocellulose, using two optional tags of the hybrid conjugate.

FIG. 6 shows the detection of a mouse monoclonal IgG dotted onto nitrocellulose, using the two optional tags of the hybrid conjugate. A total of 0.1–100 ng of antibody diluted in 100 µg/ml BSA was dotted on the nitrocellulose in duplicate. The nitrocellulose was dried, blocked with BSA and incubated with the conjugate in the presence of 0.1% Tween 20 for 20 minutes. One of the blots was transferred to the enzyme substrate (BCIP) solution and incubated as described above. The developed blots shows that 1 ng of antibody could be detected using the gold stain, while 0.1 ng was detected using the enzyme. The enzyme stain appears to give an overall increased sensitivity of about 15 times compared to the gold stain.

EXAMPLE 10

In this example is demonstrated the formation of a hybrid superaggregate containing colloidal gold and two different proteins, one of which is a specific binding partner for the analyte and the second protein not participating in the reaction, or not being present in the sample or the reagents in other ways. This hybrid superaggregate can be used to further increase the sensitivity of the assay by addition of a second superaggregate containing colloidal gold and a specific binding partner for said second protein.

Nitrocellulose membranes were coated with monoclonal antibody S4H9 (1 mg/ml), specific to the fibrin degradation product D-dimer, and the nitrocellulose was placed in a test-device as described in example 1. Preparations containing D-dimer in the concentration range 0–8 mg/L, dissolved in 0.1 mol/L Tris-HCl-buffer (pH7.4) containing 50 mg/ml BSA were applied (50 µl) and allowed to soak through the membrane. The D-dimer molecules caught by the immobilised antibody were subsequently visualised by application of 50 µl of a solution containing a superaggregate of 4 nm colloidal gold, S4H9, and human serum albumin (HSA). This superaggregate was prepared as in example 1 with a 1:1 (w/w) ratio between S4H9 and HSA. The membrane was washed and the signal strength of the colloidal gold retained on the membrane was measured using a reflectometer. A second superaggregated complex of colloidal gold and monoclonal antibody 2D2 was prepared as described in example 4. This second superaggregate was applied to the nitrocellulose, and the aggregate was immobilised by linkages between the HSA present in the first superaggregate and antibody 2D2 in the second aggregate. The membrane was washed, and the resulting signal was measured using a reflectometer. It could be demonstrated that the signal obtained after the second step was four times the strength of the signal obtained after the first step.

Figure 7:
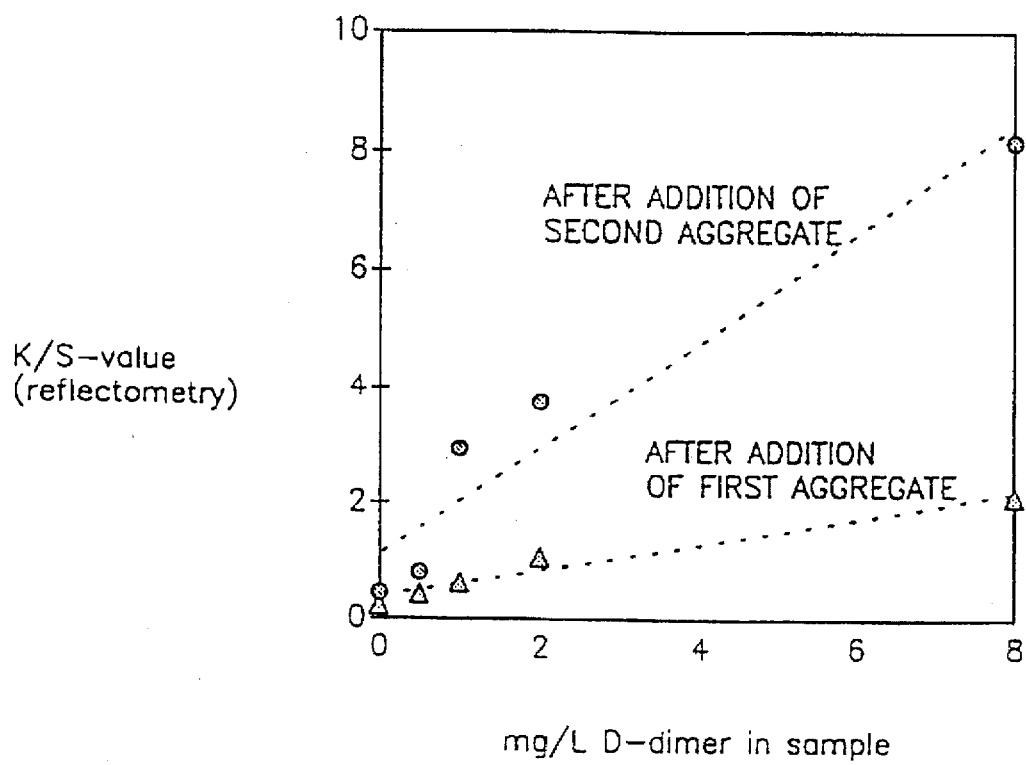
FIG. 7 illustrates the dose-response curves obtained with increasing amounts of D-dimer in the sample.

FIG. 7 illustrates the dose-response curves obtained with increasing amounts of D-dimer in the sample.

We claim:

1. In a method for the qualitative or quantitative determination of an analyte in a test sample comprising:

immobilizing a labelled reagent comprising a gold sol bound to a protein or fragment thereof specifically binding to said analyte, or a gold sol bound to a protein or fragment thereof which is a specific binding partner for a substance which specifically binds to said analyte, in bound form on a solid phase; and detecting the presence or absence of said labelled reagent thereby providing an indication of the presence or quantity of the analyte in the sample;

wherein the improvement comprises as the labelled reagent a superaggregated complex of a plurality of molecules of said protein or fragment and a plurality of particles of said gold sol wherein the superaggregated complex has a mean diameter of 50–5000 nm and wherein at least 75% by weight of the gold particles of the gold sol have a mean diameter of less than 20 nanometers, wherein the superaggregated complex is obtained by the process of:

(i) mixing said protein or fragment thereof and gold sol at a pH of 1–5, or at neutral pH provided that the gold sol is used in molar excess relative to the protein and the protein molecule exhibits at least two positively charged groups at the pH used, so as to form macroscopic aggregates;

(ii) collecting the macroscopic aggregates so formed;

(iii) resuspending the macroscopic aggregates in a pH-neutral medium, optionally with ultrasonic treatment, to form a suspension of stable superaggregated complexes.

2. A method as claimed in claim 1 comprising contacting said sample in an aqueous assay medium with (i) an analyte analogue or a specific binding partner for said analyte immobilized on a solid support and (ii) the labelled reagent comprising the superaggregated complex, thereby immobilizing a quantity of said labelled reagent on said support to provide directly or indirectly a color change indicating the presence or quantity of said analyte in the sample.

3. A method as claimed in claim 2 wherein the color change is detected by visual inspection or by a reflectometer.

4. A method as claimed in claim 1 wherein the superaggregated complex is a hybrid complex of two or more proteins at least one of which specifically binds to said analyte or is a specific binding partner for a substance which specifically binds to said analyte, including an enzyme which generates a characteristic reaction when exposed to a substrate therefor.

5. A method as claimed in claim 4 wherein the presence or quantity of analyte in the sample is detected by ELISA.

6. A method as claimed in claim 1 wherein the superaggregated complex is a hybrid complex of two or more proteins and a color amplification is obtained by addition of one or more further superaggregated complexes including a protein which specifically binds to a protein in said first hybrid complex.

7. A method as claimed in claim 1 wherein the pH in step (i) is from 3 to 4.

8. A method according to claim 1 wherein the superaggregated complex has a mean diameter of 100–200 nm.

9. A method as claimed in claim 1 wherein at least 75% by weight of the gold particles of the gold sol have a mean diameter of less than 5 nanometers.

10. A method as claimed in claim 1 wherein a competitive assay is performed.

11. A method as claimed in claim 1 wherein a sandwich assay is performed.

12. A method as claimed in claim 1 wherein the solid phase is an inert membrane which readily retains protein and which has pores which permit passage of liquid.

13. A method as claimed in claim 1 wherein the analyte is selected from the group consisting of serum proteins, glycoproteins, peptide hormones, immunoglobulins, microbicidal products, bacterial products, viral products, coagulation factors, complement proteins and fibrinogen degradation products.

14. A method as claimed in claim 13 wherein the analyte is selected from the group consisting of fibrin degradation product D2, human C-reactive protein, a creatinine kinase isoenzyme and myoglobin.

15. A process for preparing a superaggregated complex of a protein or fragment thereof and a gold sol wherein the superaggregated complex comprises a plurality of molecules of said protein or fragment and a plurality of particles of said gold sol and has a mean diameter of 50–5000 nm, wherein at least 75% by weight of the gold particles have a mean diameter of less than 20 nanometers comprising:

(i) mixing said protein or fragment thereof and gold sol at a pH of 1–5, or a neutral pH provided that the gold sol is used in molar excess relative to the protein and the protein molecule exhibits at least two positively charged groups at the pH used so as to form macroscopic aggregates;

(ii) collecting the macroscopic aggregates so formed;

(iii) resuspending the macroscopic aggregates in a pH-neutral medium, optionally with ultrasonic treatment, to form a suspension of stable superaggregated complexes.

16. A process according to claim 15 wherein the protein is whole.

17. A process as claimed in claim 15 wherein the pH in step (i) is from 3 to 4.

18. A superaggregated complex of a protein or fragment thereof and a gold sol wherein the superaggregated complex comprises a plurality of molecules of said protein or fragment and a plurality of particles of said gold sol and has a mean diameter of 50–5000 nm, and wherein at least 75% by weight of the gold particles have a mean diameter of less than 20 nanometers, wherein the complex is obtained by the process of claim 15.

19. A superaggregated complex according to claim 18 wherein the protein is whole.

20. A superaggregated complex as claimed in claim 18 which has a mean diameter of 100–200 nm.

21. A kit for the qualitative or quantitative determination of an analyte in a test sample, which kit comprises:

(a) a labelled reagent which comprises a superaggregated complex of a gold sol bound to a protein or fragment thereof specifically binding to said analyte, or a gold sol bound to a protein or fragment thereof which is a specific binding partner for a substance which specifically binds to said analyte, wherein the superaggregated complex comprises a plurality of molecules of said protein or fragment and a plurality of particles of said gold sol and has a mean diameter of 50–5000 nm, and wherein at least 75% by weight of the gold particles of the gold sol have a mean diameter of less than 20 nanometers, wherein the superaggregated complex is obtained by the process of:

(i) mixing said protein or fragment thereof and gold sol at a pH of 1–5, or at neutral pH provided that the gold sol is used in molar excess relative to the protein and the protein molecule exhibits at least two positively charged groups at the pH used, so as to form macroscopic aggregates;

(ii) collecting the macroscopic aggregates so formed:

(iii) resuspending the macroscopic aggregates in a pH-neutral medium, optionally with ultrasonic treatment, to form a suspension of stable superaggregated complexes; and (b) a solid phase support serving to immobilize at least a portion of said labelled reagent during determination of the analyte.

22. A kit as claimed in claim 21 wherein the pH in step (i) is from 3 to 4.

23. A kit as claimed in claim 21 wherein the solid phase system is a plastic stick which is optionally covered with pads of porous material, a test tube, a microtitre plate, a membrane, or beads which may optionally be magnetic.

24. A kit as claimed in claim 21 wherein the superaggregated complex further comprises an enzyme which generates a characteristic reaction when exposed to a substrate, the kit further comprising a substrate for said enzyme.

25. A method as claimed in claim 1 wherein said solid phase is a membrane, an absorbent pad is located on said membrane, a liquid impermeable sheet is located on the face of said absorbent pad remote from said membrane, and a liquid impermeable sheet having one or more holes therein is located on the face of said membrane remote from said absorbent pad, whereby the test sample and reagent are applied successively to one of said holes and are caused to diffuse transversely through said membrane support by absorption into said absorbent pad.

26. A kit as claimed in claim 21 wherein said solid phase support is a membrane, an absorbent pad is located on said membrane, a liquid impermeable sheet is located on the face of said absorbent pad remote from said membrane and a liquid impermeable sheet having one or more holes therein is located on the face of said membrane remote from said absorbent pad, said absorbent pad effective to cause transverse diffusion of said test sample or labelled reagent through said membrane when applied to one of said holes.

* * * * *